(12) United States Patent
Patel et al.

(10) Patent No.: US 7,069,744 B2
(45) Date of Patent: Jul. 4, 2006

(54) LEAN REFLUX-HIGH HYDROCARBON RECOVERY PROCESS

(75) Inventors: Sanjiv N. Patel, Sugar Land, TX (US); Jorge H. Foglietta, Missouri City, TX (US)

(73) Assignee: ABB Lummus Global Inc., Houston, TX (US)

(*) Notice: Subject to any disclaimer, the term of this patent is extended or adjusted under 35 U.S.C. 154(b) by 398 days.

(21) Appl. No.: 10/739,885

(22) Filed: Dec. 18, 2003

(65) Prior Publication Data

US 2004/0148964 A1    Aug. 5, 2004

Related U.S. Application Data

(60) Provisional application No. 60/435,119, filed on Dec. 19, 2002.

(51) Int. Cl.
*F25J 3/00*    (2006.01)

(52) U.S. Cl. ............................ 62/620; 62/630

(58) Field of Classification Search ................ 62/620, 62/630
See application file for complete search history.

(56) References Cited

U.S. PATENT DOCUMENTS

| | | | |
|---|---|---|---|
| 4,157,904 A | 6/1979 | Campbell et al. | |
| 4,171,964 A * | 10/1979 | Campbell et al. | 62/621 |
| 4,278,457 A | 7/1981 | Campbell et al. | |
| 4,519,824 A | 5/1985 | Huebel | |
| 4,689,063 A | 8/1987 | Paradowski et al. | |
| 4,690,702 A | 9/1987 | Paradowski et al. | |
| 4,854,955 A | 8/1989 | Campbell et al. | |
| 5,771,712 A | 6/1998 | Campbell et al. | |
| 5,992,175 A * | 11/1999 | Yao et al. | 62/621 |
| 6,244,070 B1 | 6/2001 | Lee et al. | |
| 6,354,105 B1 | 3/2002 | Lee et al. | |
| 6,401,486 B1 | 6/2002 | Lee et al. | |
| 6,425,266 B1 * | 7/2002 | Roberts | 62/621 |
| 6,516,631 B1 | 2/2003 | Trebble | |
| 6,823,692 B1 * | 11/2004 | Patel et al. | 62/620 |
| 2002/0157538 A1 | 10/2002 | Foglietta et al. | |
| 2003/0221447 A1 | 12/2003 | Mealey | |

* cited by examiner

*Primary Examiner*—Melvin Jones
(74) *Attorney, Agent, or Firm*—Bracewell & Giuliani LLP

(57) ABSTRACT

A two-tower scheme process for the recovery of propane and heavier components from a hydrocarbon gas stream is provided. Feed gas is cooled, partially condensed, and then separated to give a first liquid stream and a first vapor stream. First liquid stream is sent to a distillation tower that recovers at the bottoms a major portion of propane and heavier components and produces an overhead gas stream. First vapor stream is expanded and sent as bottom feed to the absorber. Absorber produces an absorber overhead stream containing essentially all the ethane and lighter components and an absorber bottoms stream. Absorber bottoms stream is heated and sent to the distillation tower as middle feed. Absorber overhead stream is warmed and optionally compressed. A part of the compressed stream is substantially condensed and sent to absorber as top feed. The process and apparatus can be used to recover ethane and heavier hydrocarbons.

45 Claims, 9 Drawing Sheets

LEAN REFLUX-HIGH HYDROCARBON RECOVERY PROCESS

RELATED APPLICATIONS

This patent application claims priority to U.S. Provisional Patent Application Serial No. 60/435,119 filed on Dec. 19, 2002, which is incorporated by reference in its entirety.

BACKGROUND OF THE INVENTION

1. Technical Field of the Invention

The present invention relates to the recovery of hydrocarbons from natural gas. More particularly, the invention relates to the recovery of ethane, propane, and heavier compounds from gas streams utilizing a lean reflux stream.

2. Description of the Related Art

Valuable hydrocarbon components, such as ethane, ethylene, propane, propylene and heavier hydrocarbon components, are present in a variety of gas streams. Some of the gas streams are natural gas streams, refinery off gas streams, coal seam gas streams, and the like. In addition these components may also be present in other sources of hydrocarbons such as coal, tar sands, and crude oil to name a few. The amount of valuable hydrocarbons varies with the feed source. The present invention is concerned with the recovery of valuable hydrocarbon from a gas stream containing more than 50% methane and lighter compounds [i.e., nitrogen, carbon monoxide (CO), hydrogen, etc.], ethane, and carbon dioxide ($CO_2$). Propane, propylene and heavier hydrocarbon components generally make up a small amount of the overall feed. Due to the cyclical fluctuation of prices of natural gas and corresponding natural gas liquids (NGL), i.e., the hydrocarbon components recovered from natural gas in liquid form, processes need to be developed that can run under both ethane recovery and propane recovery modes of operation. In addition, these processes need to be easy to operate and be efficient in order to maximize the revenue generated from the sale of NGL.

Several processes are available to recover hydrocarbon components from natural gas. These include refrigeration processes, lean oil processes, refrigerated lean oil processes and cryogenic processes. Of late, cryogenic processes have largely been preferred over other processes due to better reliability, efficiency, and ease of operation. Depending on the desired hydrocarbon components to be recovered, i.e. ethane and heavier components or propane and heavier components, the cryogenic processes are different. Typically, ethane recovery processes employ a single tower with reflux to increase recovery and make the process efficient, such as illustrated in U.S. Pat. No. 4,519,824 issued to Huebel; U.S. Pat. No. 4,278,457 issued to Campbell et al.; and U.S. Pat. No. 4,157,904 issued to Campbell et al.

However, when ethane prices are not favorable to justify ethane recovery in NGL, the ethane component needs to be rejected while still maintaining high propane and heavier component recovery. The single tower ethane recovery schemes mentioned above can reject ethane, but these schemes start to loose propane and heavier components as ethane rejection increases. In order for a process to easily reject ethane while recovering most of the propane and heavier components, a propane recovery process needs to be considered. Most high propane recovery processes consist of two towers, typically with one tower being an absorber column and the other being a deethanizer column. This two tower scheme rejects essentially all the ethane, while recovering a large portion of propane and heavier components. In order for the process to recover 99% of the propane and heavier components, the absorber column is provided with an additional lean reflux stream. This lean reflux stream is responsible for essentially complete recovery of propane. An example two-tower scheme for propane recovery can be seen in U.S. Pat. No. 5,771,712 issued to Campbell et al (hereinafter referred to as "the '712 patent").

The '712 patent describes processes that use a two tower scheme for propane recovery with FIGS. 4 and 5 of the '712 patent being the preferred embodiments. The propane recovery schemes described in the '712 patent can be more economical to build. For example, FIG. 6 of the '712 patent is an embodiment that eliminates the reflux system from the preferred embodiments to reduce capital cost. However, significant efficiency is lost in the process and this scheme has a limitation in that the propane recovery is less than 99%.

A need exists for a propane recover process that is capable of recovering greater than 99% propane without an increase in compression power, when compared with comparable processes. It would be desirable if the process could be constructed so that there is a reduction in capital costs, such as by eliminating a reflux system.

SUMMARY OF THE INVENTION

The present invention includes a process and apparatus to increase the recovery of ethane, propane, and heavier compounds from a hydrocarbon gas stream. The present invention can be configured to recovery ethane and heavier compounds or propane and heavier compounds, depending upon the market conditions.

For propane recovery, an inlet gas stream is cooled and sent to a cold, or first, separator that is used to separate the inlet gas stream into a first liquid stream and a first vapor stream. First, liquid stream is warmed, partially vaporized, and then sent to a distillation tower. The distillation tower can be a demethanizer if ethane is being recovered or a deethanizer if propane is being recovered. First vapor stream is expanded and sent to an absorber column. Absorber column produces an absorber overhead stream and an absorber bottoms stream. Absorber bottoms stream is warmed to recover refrigeration from the process and then sent to distillation tower. Distillation tower produces a tower overhead stream and a tower bottoms stream. Tower overhead stream is at least partially condensed and is sent as first lean reflux stream to absorber column. A second lean reflux stream can be taken as a side stream of a residue gas stream or as a side stream of the first vapor stream from the cold separator. Absorber column preferably contains at least one mass transfer zone when the second lean reflux stream is taken as a side stream of the residue gas stream. The absorber contains at least one or more mass transfer zones (preferably two) when the second lean reflux stream is taken from the cold separator vapor stream. The result of this cryogenic process is an increase in the amount of $C_3+$ compounds that is recovered from an inlet gas stream with only a slight increase in the residue gas compression requirements, as compared with other propane recovery processes.

The propane recovery process can be simplified as another embodiment of the present invention. In this alternate embodiment, the deethanizer reflux accumulator, or second separator, and pumps can be removed and the absorber bottoms stream can be split into two streams, a first absorber bottoms stream and a second absorber bottoms stream. First absorber bottoms stream is sent directly to a top of distillation tower as a third tower feed stream, while second absorber bottoms stream is heated and sent lower in the distillation tower as a second deethanizer feed stream.

One embodiment of the present invention can also be used to recover ethane and heavier compounds. As in the propane recovery embodiments, an inlet gas stream is cooled and sent to cold separator, where the inlet gas stream is separated into first liquid stream and first vapor stream. First liquid stream can be sent directly to distillation tower as a lower feed stream. First vapor stream can be split into two streams, a first separator overhead stream and a second separator overhead stream. First separator overhead stream is expanded and sent to an absorber column. A preferred embodiment of absorber column has two mass transfer zones and the second separator overhead stream can be sent between the two mass transfer zones. Absorber bottoms stream is sent to distillation tower as a top tower feed stream. Distillation tower produces a tower overhead stream and a tower bottoms stream. Tower overhead stream is sent to a condenser, or reflux exchanger, to condense the hydrocarbons and then is sent to absorber column as a top absorber feed stream. Tower bottoms stream contains the NGL stream product. The result of this cryogenic process is an increase in the amount of $C_2+$ compounds that is recovered from an inlet gas stream with only a slight increase in the residue gas compression requirements as compared with other ethane recovery processes.

In addition to method embodiments, the apparatus to perform the methods described herein are advantageously provided. The apparatus for separating an inlet gas stream containing methane, C2 and C3 components and heavier hydrocarbons into a volatile gas fraction containing substantially all of the methane and C2 components and a less volatile fraction containing a large portion of C3 components and heavier hydrocarbons preferably includes a first exchanger, a first separator, a distillation tower, a second exchanger, an expander, and a compressor.

First exchanger, or inlet exchanger, is utilized for performing a process step selected from the group consisting of cooling inlet gas stream to partially condense at least a portion of inlet gas stream, preheating at least a portion of first liquid stream, preheating at least a portion of absorber bottoms stream, heating absorber overhead stream, cooling and at least partially condensing the portion of residue gas stream thereby producing second lean reflux stream, and combinations thereof.

First separator is used for separating inlet gas stream into first vapor stream and at least first liquid stream. Distillation tower is used for receiving a portion of first liquid stream as lower tower feed stream and for receiving a portion of absorber bottoms stream as a middle tower feed stream. Distillation tower advantageously produces tower overhead stream containing mainly methane and C2 components and tower bottoms stream containing a majority of the C3 components and heavier hydrocarbons.

Second exchanger, or reflux exchanger, is for performing a process step selected from the group consisting of cooling tower overhead stream thereby producing second vapor stream and liquid hydrocarbon stream, cooling and condensing at least a portion of second vapor stream thereby forming first lean reflux stream, heating absorber overhead stream, cooling and at least partially condensing the portion of residue gas stream thereby producing second lean reflux stream.

Expander preferably expands first vapor stream. Absorber column preferably has at least one mass transfer zone. Absorber column receives first vapor stream as a bottom absorber feed stream, first lean reflux stream as an absorber top feed stream, and second lean reflux stream. Absorber column produces absorber overhead stream containing essentially all methane, C2 and lighter components of the gas stream and absorber bottoms stream.

Compressor is preferably used to compress absorber overhead stream to produce residue gas stream. Second separator, or reflux accumulator, separates the tower overhead stream into a second vapor stream and a liquid hydrocarbon stream.

BRIEF DESCRIPTION OF THE DRAWINGS

So that the manner in which the features, advantages and objects of the invention, as well as others which will become apparent, may be understood in more detail, more particular description of the invention briefly summarized above may be had by reference to the embodiment thereof that is illustrated in the appended drawings, which form a part of this specification. It is to be noted, however, that the drawings illustrate only a preferred embodiment of the invention and are therefore not to be considered limiting of the invention's scope as it may admit to other equally effective embodiments.

DETAILED DESCRIPTION OF THE DRAWINGS

Figure 1:
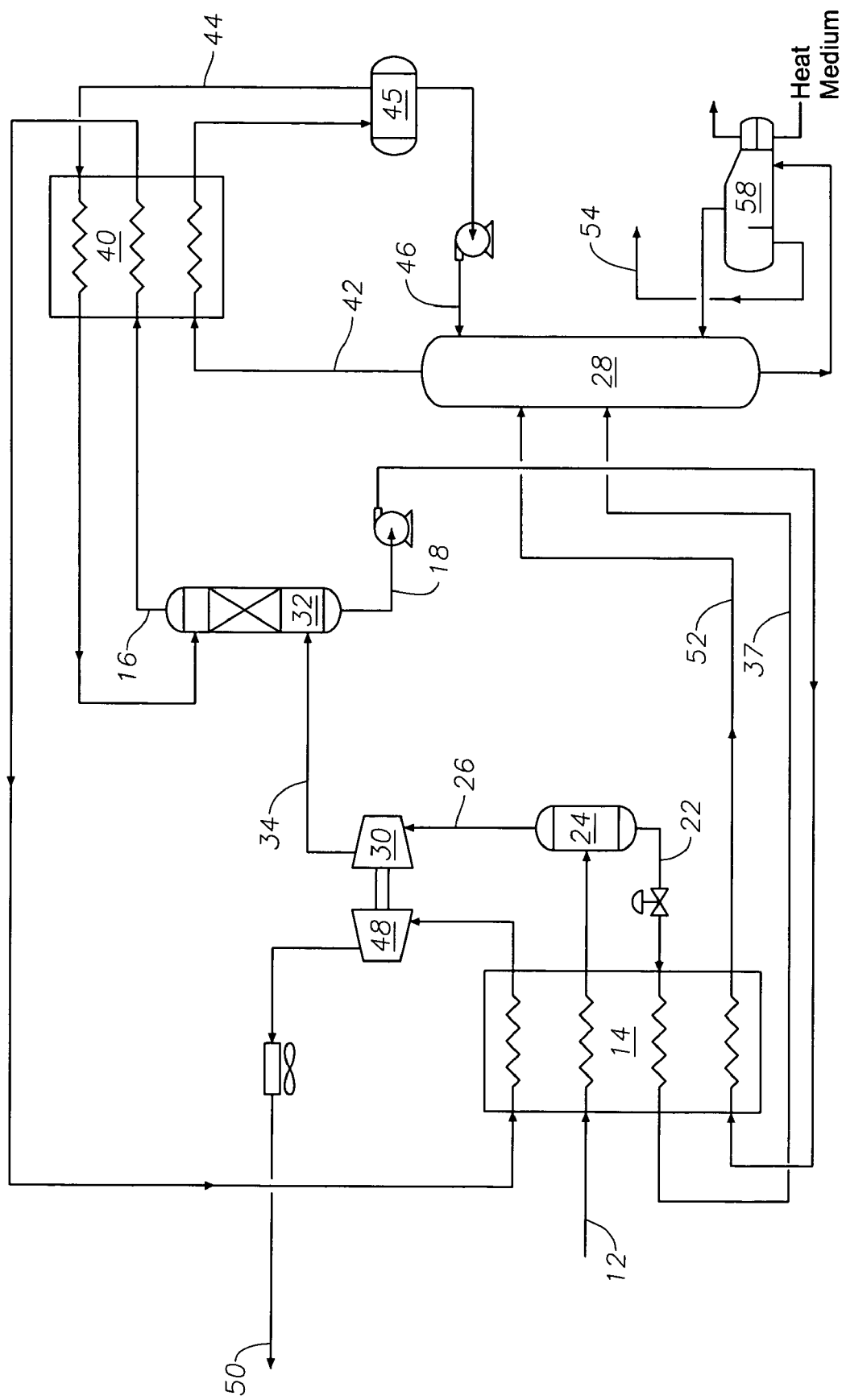
FIG. 1 is a simplified flow diagram of a prior art process as shown in U.S. Pat. No. 4,690,702 issued to Paradowski et al., which illustrates a typical two tower process for propane recovery.

In the drawings, figure numbers are the same in the figures for various streams and equipment when the functions are the same, with respect to the streams or equipment. Like numbers refer to like elements throughout, and prime, double prime, and triple prime notation, where used, generally indicate similar elements in alternative embodiments.

As used herein, the term "inlet gas" means a hydrocarbon gas. Such gas is typically received from a high pressure gas line and is substantially comprised of methane, with the balance being C2 compounds, C3 compounds and heavier compounds as well as carbon dioxide, nitrogen and other trace gases. The term "C3+ compounds" means all organic compounds having three or more carbon atoms, including aliphatic species such as alkanes, olefins, and alkynes, and, in particular, propane, propylene, methyl-acetylene and the like.

DETAILED DESCRIPTION OF FIRST PRIOR ART EXAMPLE

FIG. 1 illustrates a typical prior art scheme as described in U.S. Pat. No. 4,690,702 issued to Paradowski, et al., which includes a two tower scheme that is used for high propane recovery. To illustrate the improvements achieved with using the present invention, a typical inlet gas composition has been provided in Table I. Inlet gas having a composition similar to that contained in Table I can be used in the Paradowski process shown in FIG. 1.

TABLE I

| Component | Mol % |
| --- | --- |
| N2 | 0.166 |
| CO2 | 6.280 |
| Methane | 77.391 |
| Ethane | 9.128 |
| Propane | 4.238 |
| i-Butane | 0.723 |
| n-Butane | 1.124 |
| i-Pentane | 0.323 |
| n-Pentane | 0.276 |
| n-Hexane | 0.213 |
| n-Heptane | 0.130 |
| n-Octane | 0.007 |
| Temperature (° F.) | 108.8 |
| Pressure (psia) | 1075 |
| Flow (MMSCFD) | 399.99 |

Raw feed gas to the plant can contain certain materials that are detrimental to cryogenic processing. These impurities include water, CO2, H2S, and other impurities. It is assumed that raw feed gas is treated to remove CO2 and H2S, if they are present in large quantities. The gas is then dried and filtered before being sent to the cryogenic section for NGL recovery. Clean and dry feed gas (12) at 108° F. and 1075 psia is cooled in inlet exchanger (14) against cold process streams to 10° F. and sent to cold separator (24) for phase separation. Liquid stream (22) from the cold separator is withdrawn, flashed from 1060 psia to 420 psia pressure across a control valve and then preheated in inlet exchanger. Heated and partially vaporized stream (37) at 100° F. exiting the exchanger is then sent to deethanizer (28) as lower feed. Vapor stream (26) leaving the cold separator is sent to an expander (30) for isentropic expansion to 365 psia. Due to the reduction in pressure and extraction of work from the high pressure stream, stream (34) leaving the expander is cooled to −69° F., which partially condenses stream (34). Stream (34) is then sent to the bottom of absorber column (32). The absorber column is a trayed or packed column that operates at 358 psia. Absorber overhead stream is lean residue gas (16) at −87° F. and absorber bottoms stream (18) is hydrocarbon stream at −72° F. Absorber bottoms stream, which contains methane, ethane, propane and heavier components, is pumped to a higher pressure and then preheated in inlet exchanger to −10° F. to form a two phase stream (52). Stream (52) is then sent to distillation tower as a middle tower feed stream;

Distillation tower is a trayed or packed tower that operates at 395 psia. Distillation tower recovers at the bottom of the distillation tower, stream (54), which contains a majority of propane, propylene and heavier components from the feed gas. Tower overhead stream (42) is partially condensed in reflux exchanger (40) by cooling to −23° F. and is then sent to the reflux accumulator, or second separator, for phase separation. Liquid reflux stream (46) is pumped back to the distillation tower as reflux stream. Distillation tower is provided with a reboiler (58) that provides the required heating duty at the bottom of the distillation tower.

Stream (44) leaving the reflux accumulator is condensed as much as possible in the reflux accumulator by cooling to −81° F. This cold and partially condensed stream is then sent to absorber column as a top absorber feed stream. Absorber overhead stream is warmed in the reflux exchanger, or second exchanger, to −22° F., and then further heated in inlet exchanger to 96° F. Warmed low pressure residue gas stream leaving the exchanger is boosted in pressure to 461 psia by booster compressor (48) that runs off of the power generated by expander (30). Intermediate pressure residue gas stream is cooled to ambient conditions, and then boosted to 1140 psia in residue compressors (49). Hot high pressure residue gas stream is cooled to ambient temperature and sent for further processing as stream (50). Table II presents the results of running a simulation for the process shown in FIG. 1 that utilizing an inlet gas stream having the composition shown in Table I.

TABLE II

| | Mol % | | |
| --- | --- | --- | --- |
| Component | Feed | Residue | NGL |
| Nitrogen | 0.166 | 0.178 | 0.000 |
| CO2 | 6.280 | 6.746 | 0.001 |
| Methane | 77.391 | 83.132 | 0.000 |
| Ethane | 9.128 | 9.727 | 1.053 |
| Propane | 4.238 | 0.216 | 58.450 |
| i-Butane | 0.723 | 0.000 | 10.468 |
| n-Butane | 1.124 | 0.000 | 16.276 |
| i-Pentane | 0.323 | 0.000 | 4.677 |
| n-Pentane | 0.276 | 0.000 | 3.997 |
| n-Hexane | 0.213 | 0.000 | 3.079 |
| n-Heptane | 0.130 | 0.000 | 1.882 |
| n-Octane | 0.007 | 0.000 | 0.103 |
| Mol/hr | 43918.6 | 40886 | 3033 |
| Temperature (° F.) | 108.8 | 120 | 204 |
| Pressure (psia) | 1075 | 1135 | 395 |
| C3 Recovery (%) | 95.25 | | |
| Residue Compression (hp) | 23660 | | |

DETAILED DESCRIPTION OF THE PRESENT INVENTION

Figure 2:
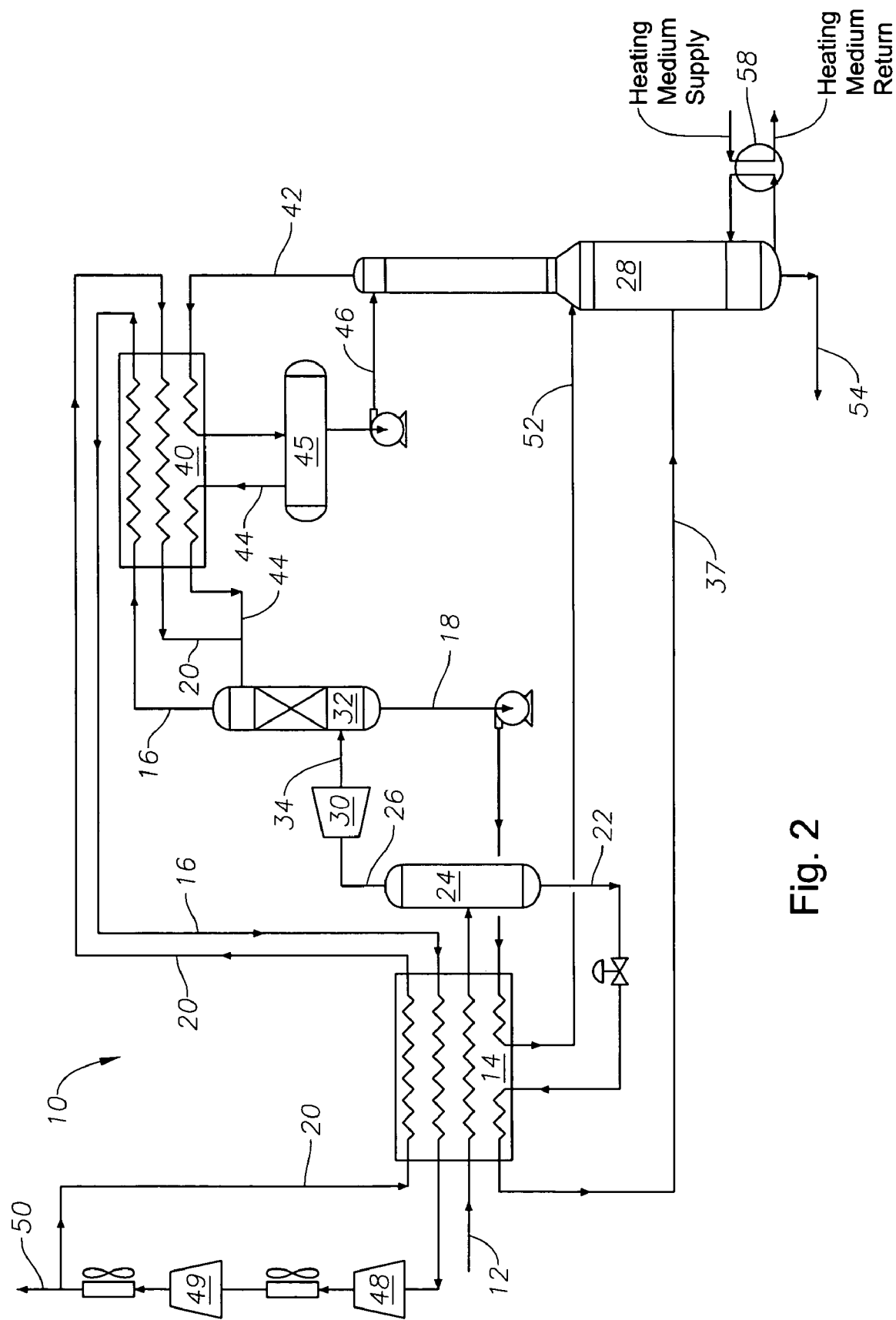
FIG. 2 is a simplified flow diagram of an C3+ compound recovery process that incorporates the improvements of the present invention and is configured for increased recovery of C3+ from an inlet gas stream through the use of the absorber second lean reflux stream in accordance with an embodiment of the present invention.

FIG. 2 illustrates one embodiment of the improved C3+ compound recovery scheme 10. Inlet gas stream 12 is cooled to 9.5° F. in inlet, or first, exchanger 14 by heat exchange contact with cold streams to cool and partially condense the inlet gas stream 12. Inlet gas stream 12 can have the same composition as that shown in Table I. Suitable cold streams that can be used to cool inlet gas stream 12 can include an absorber overhead stream, an absorber bottoms stream, a first liquid stream, external refrigerants, and combinations thereof. In all embodiments of this invention, inlet exchanger 14 is preferably a single multi-path exchanger, a plurality of individual heat exchangers, or combinations thereof. Inlet gas stream 12 is supplied to cold, or first, separator 24 where a first vapor stream 26 is separated from a first liquid stream 22.

In all embodiments of the present invention, if propane recovery is desired, a deethanizer tower can be used as the distillation tower. If ethane recovery is desired, then a demethanizer tower can be used as the distillation tower.

First liquid stream 22 is reduced in pressure to 420 psia whereby it is partially vaporized, and cooled to −28° F. The two phase stream is heated to 100° F. in inlet exchanger 14 and sent to distillation tower 28 as first tower feed stream 37. First vapor stream 26 is expanded isentropically in an expander 30 where its pressure is reduced to 367 psia. Due to the reduction in pressure and extraction of work, the resulting stream 34 is cooled to −70° F. and partially condensed. Stream 34 is sent to an absorber column 32, preferably at the bottom of the absorber column 32, as first absorber feed stream. In absorber column 32, which operates at 360 psia, the rising vapors in first absorber feed stream 34 are at least partially condensed by intimate contact with falling liquids thereby producing an absorber overhead stream 16 at −90° F. that contains substantially all of the methane, C2 compounds and lighter compounds in the first absorber feed stream 34. Absorber 32 contains at least one mass transfer zone. In all embodiments of the present invention, the mass transfer zone can be a flash zone, an equilibrium stage, packing section, tray, or the like. The condensed liquids descend down the absorber column 32 and are removed as absorber bottoms stream 18 at −72° F., which contains some methane, ethane, propane and heavier components. Absorber bottoms stream 18 is supplied, preferably by pumping to inlet exchanger 14, where absorber bottoms stream 18 is heated to −5° F. in inlet exchanger 14 and then sent to the distillation tower 28 as a middle deethanizer feed stream 52.

Distillation tower 28 is preferably a trayed or packed tower that operates at 395 psia. Distillation tower 28 recovers at the bottom of the tower, stream 54, which contains a majority of propane, propylene, and heavier components from feed gas stream 12. Tower overhead stream 42 is partially condensed in reflux exchanger 40 by cooling to −31° F. and sent to reflux accumulator, or second separator, 45 for phase separation. Liquid reflux stream 46 is pumped back to distillation tower 28 as reflux stream. Distillation tower 28 is provided with a bottom reboiler 58 that provides heating duty at the bottom of distillation tower 28.

Stream 44 leaving reflux accumulator 45 is condensed as much as possible in reflux exchanger 40 by cooling stream 44 to −85° F. This cold and partially condensed stream 44 is then sent to absorber column 32 as a feed stream. Cold residue gas, or absorber overhead stream, 16 leaving absorber column 32 is warmed in reflux exchanger 40 to −16° F., and then further heated in inlet exchanger 14 to 101° F. Warmed low pressure residue gas 16 leaving exchanger 14 is boosted in pressure to 465 psia by booster compressor 48 that runs off of the power generated by expander 30. Intermediate pressure residue gas is cooled to ambient conditions, and then boosted to 1140 psia in residue compressors 49. Hot high pressure residue gas is cooled to ambient temperature and sent for further processing as residue gas stream 50. A second lean reflux stream 20 is sent to absorber column 32 that is leaner in ethane and propane than deethanizer overhead stream 42. Second lean reflux stream 20 can be taken as a side stream from the residue gas stream 50, as shown in FIG. 2. Second lean reflux stream 20 is cooled in inlet exchanger 14 and then condensed in reflux exchanger 40. The resulting condensed liquid is then fed to absorber column 32 to enhance the amount of $C_3+$ compounds recovered. First and second lean reflux streams 20, 44 can be combined prior to being sent to absorber column 32.

A simulation was performed using the process illustrated in FIG. 2 and an inlet gas having a composition shown in Table I. The results of the simulation for this embodiment of the present invention are shown in Table III.

TABLE III

| Component | Mol % | | |
|---|---|---|---|
| | Feed | Residue | NGL |
| Nitrogen | 0.166 | 0.179 | 0.000 |
| CO2 | 6.280 | 6.758 | 0.001 |
| Methane | 77.391 | 83.289 | 0.000 |
| Ethane | 9.128 | 9.742 | 1.071 |
| Propane | 4.238 | 0.032 | 59.432 |
| i-Butane | 0.723 | 0.000 | 10.210 |
| n-Butane | 1.124 | 0.000 | 15.873 |
| i-Pentane | 0.323 | 0.000 | 4.561 |
| n-Pentane | 0.276 | 0.000 | 3.898 |
| n-Hexane | 0.213 | 0.000 | 3.002 |
| n-Heptane | 0.130 | 0.000 | 1.836 |
| n-Octane | 0.007 | 0.000 | 0.100 |
| Mol/hr | 43918.6 | 40809 | 3110 |
| Temperature (° F.) | 108.8 | 120 | 203 |
| Pressure (psia) | 1075 | 1135 | 395 |
| C3 Recovery (%) | 99.3 | | |
| Residue Compression (hp) | 23930 | | |

Figure 3:
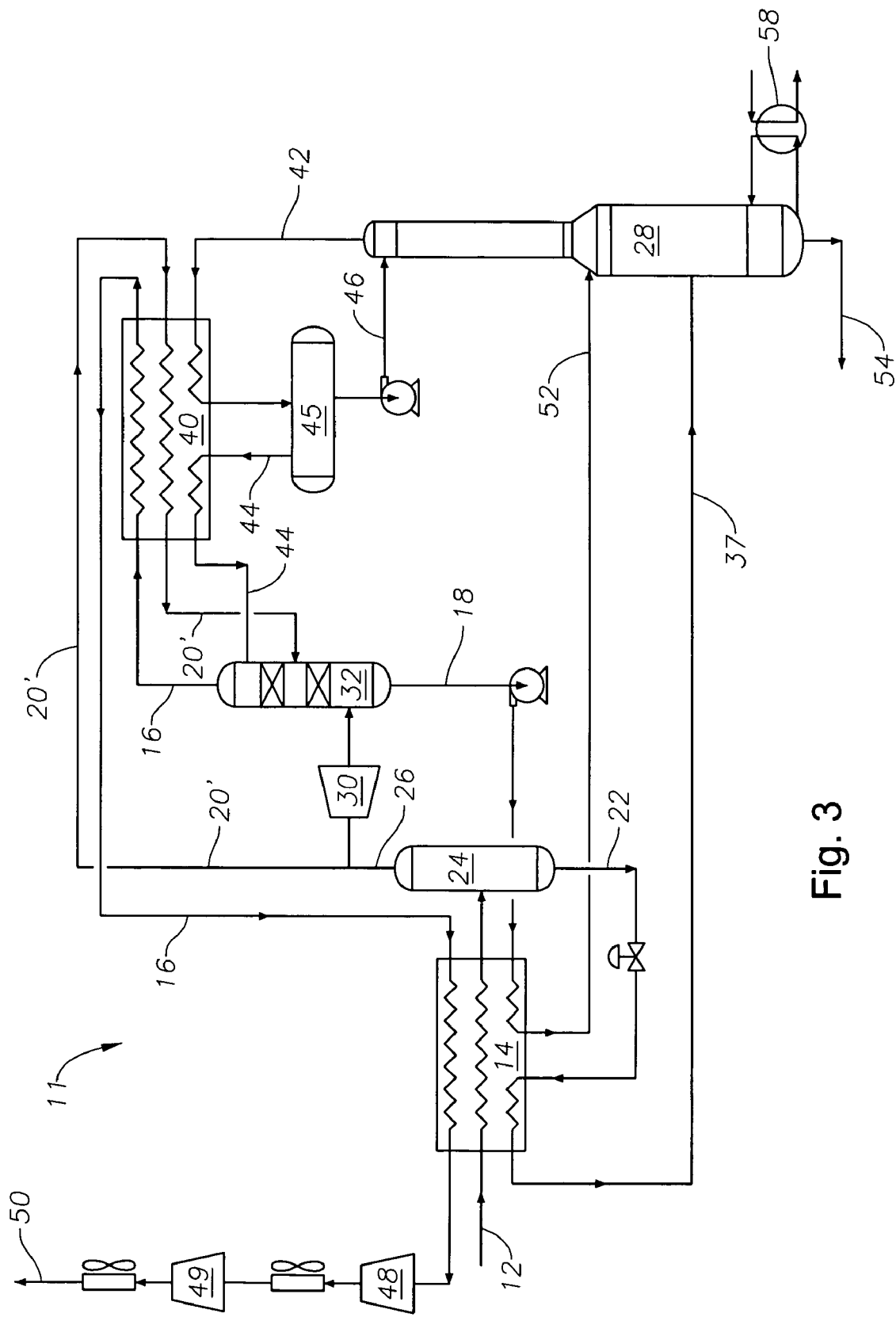
FIG. 3 is a simplified flow diagram of an C3+ compound recovery process that incorporates the improvements of the present invention and is configured for increased recovery of C3+ compounds through the use of an alternate absorber second lean reflux stream in accordance with an embodiment of the present invention.

FIG. 3 depicts an alternate embodiment for the C3+ recovery process 11 wherein the second lean reflux stream 20' is taken from at least a portion of first vapor stream 26. Absorber column 32 contains one or more mass transfer zones (preferably two) in this embodiment. Second lean reflux stream 20' is sent to absorber column 32 between the mass transfer zones when there is more than one mass transfer zone.

A simulation was performed using the process illustrated in FIG. 3 and an inlet gas having a composition shown in Table I. The results of the simulation for this embodiment of the present invention are shown in Table IV.

TABLE IV

| Component | Mol % | | |
|---|---|---|---|
| | Feed | Residue | NGL |
| Nitrogen | 0.166 | 0.179 | 0.000 |
| CO2 | 6.280 | 6.757 | 0.001 |
| Methane | 77.391 | 83.276 | 0.000 |
| Ethane | 9.128 | 9.741 | 1.069 |
| Propane | 4.238 | 0.046 | 59.356 |
| i-Butane | 0.723 | 0.000 | 10.230 |
| n-Butane | 1.124 | 0.000 | 15.904 |
| i-Pentane | 0.323 | 0.000 | 4.570 |
| n-Pentane | 0.276 | 0.000 | 3.905 |
| n-Hexane | 0.213 | 0.000 | 3.008 |
| n-Heptane | 0.130 | 0.000 | 1.839 |
| n-Octane | 0.007 | 0.000 | 0.100 |

TABLE IV-continued

|  | Mol % | | |
| --- | --- | --- | --- |
| Component | Feed | Residue | NGL |
| Mol/hr | 43918.6 | 40815 | 3104 |
| Temperature (° F.) | 108.8 | 120 | 204 |
| Pressure (psia) | 1075 | 1135 | 398 |
| C3 Recovery (%) |  | 99.0 |  |
| Residue Compression (hp) |  | 23740 |  |

An advantage of this embodiment of the present invention is the increase in the recovery of $C_3$ from 95.3% to 99.3% with the addition of the second lean reflux stream 20, when the second lean reflux stream 20 is taken as a side stream of the residue gas stream 50, as shown in FIG. 2. Compression power increases by 1.1%. When the second reflux stream 20' is taken as a side stream of the first vapor stream 26, as shown in FIG. 3, the recovery of $C_3+$ increases from 95.3% to 99%. The compression requirements for the residue gas stream 50 will increase by 0.3% when compared to a typical gas plant process without second lean reflux stream. It can be seen that for a negligible change in compression power, the recovery of propane can be increased to 99+ %. Generally, residue gas compression equipment has the required additional capacity to make the processes described herein work, without the need to purchase new compression equipment or alter the existing compression equipment.

A continuous trend in the gas processing industry is to make processes more efficient and reduce capital expense. In order to make the two tower scheme shown in FIG. 2 more economical to construct, the scheme can be modified to eliminate the reflux system on distillation tower 28, as shown in FIG. 4.

Figure 4:
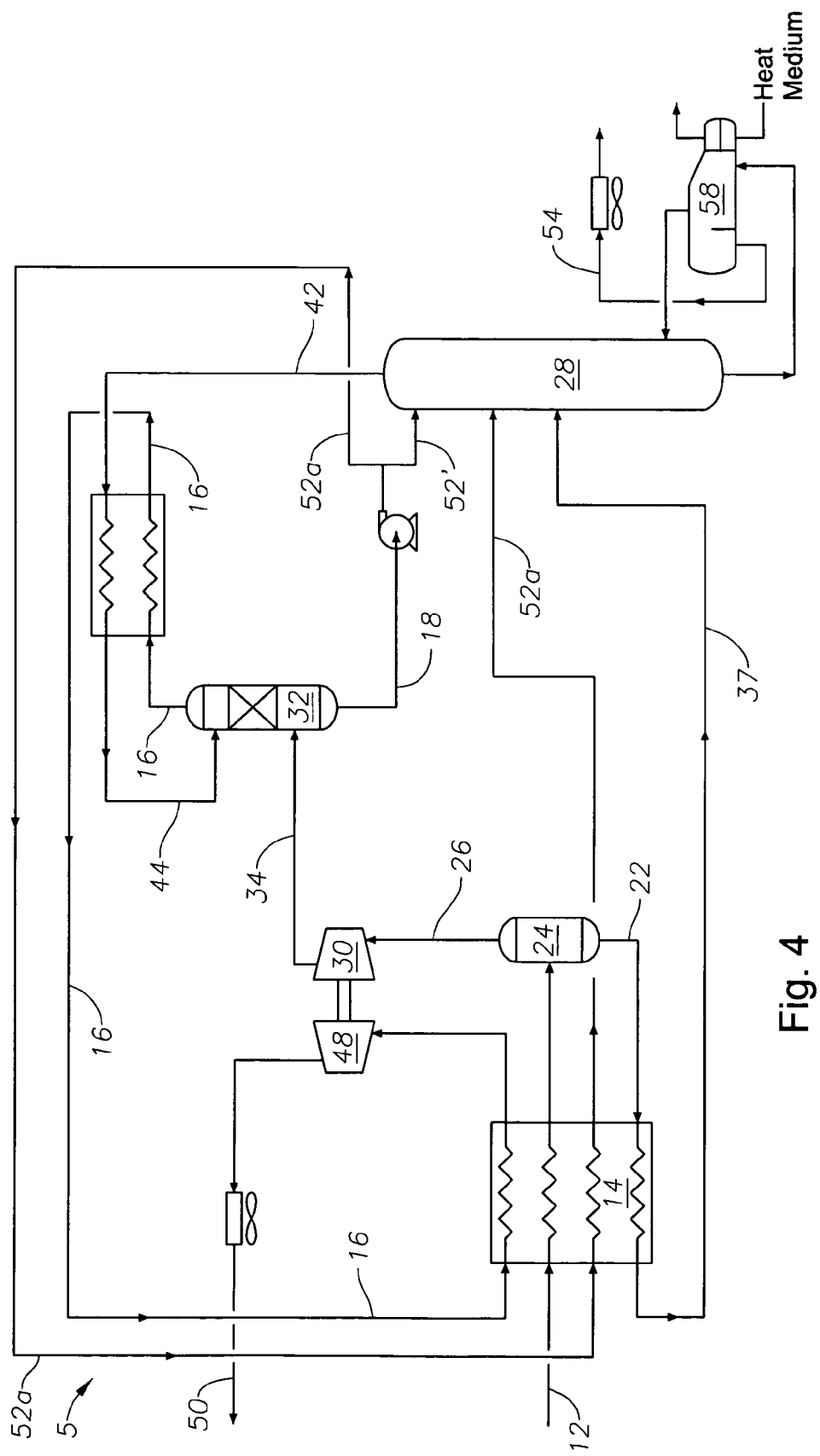
FIG. 4 is a simplified flow diagram of a C3+ compound recovery process that incorporates the simplification of the system under the present invention and is configured for increased recovery of C3+ from an inlet gas stream according to one embodiment of the present invention.

As shown in FIG. 4, the new process involves splitting absorber bottoms stream into two streams 52a, 52'. One stream 52a is heated in inlet exchanger 14 and sent to distillation tower 28 as a middle tower feed stream. The other stream 52' is sent directly to the top of distillation tower 28 as a top tower feed stream. Sending the cold liquid stream 52' at the top of distillation tower 28 prevents significant loss of C3+ from the deethanizer overhead stream 42, while the other portion of the absorber bottoms, stream 52a, is heated against inlet gas stream 12 to recover cooling. This split of absorber bottoms stream 18 keeps deethanizer overhead stream lean in C3, thereby providing good reflux for absorber column 32, and consequently a more efficient process.

In FIG. 4, inlet gas stream 12 entering at 80° F. and 580 psia is cooled in inlet exchanger 14 to −78° F. thereby partially condensing inlet gas stream 12. Inlet gas stream 12 is supplied to a cold separator, or first separator, 24 where a first vapor stream 26 is separated from a first liquid stream 22.

First liquid stream 22 is reduced in pressure to 425 psia whereby it is cooled to −93° F. and partially vaporized. This resulting two phase stream 22 is heated to 75° F. in the inlet, or first, exchanger 14, wherein the stream is further vaporized, and sent to a deethanizer tower 28 as a bottom deethanizer feed stream 37. First vapor stream 26 is isentropically expanded in an expander 30 where its pressure is reduced to 398 psia to produce expanded stream 34. Due to reduction in the pressure and extraction of work from stream 26, expanded stream 34 exiting the expander is cooled to −107° F. thereby partially condensing stream 34. Stream 34 is sent to an absorber column 32, preferably at the bottom of absorber column 32, as first absorber feed stream 34. In absorber column 32, the rising vapors of the first absorber feed stream 34 are at least partially condensed by intimate contact with the falling liquids from the first lean reflux stream 44 thereby producing an absorber overhead stream 16 that contains substantially all of the methane and $C_2$ compounds and lighter compounds in the first absorber feed stream 34.

Absorber column 32 contains at least one mass transfer zone. The mass transfer zone can be a flash zone, an equilibrium stage, or the like. Absorber column 32 operates at 398 psia. The condensed liquids descend down absorber column 32 and are removed as absorber bottom stream 18 at −108° F., which contains some methane, ethane, propane and heavier components. Absorber bottoms stream 18 is pumped to a higher pressure, and split into two streams, with 60% of absorber bottoms stream 18 forming a first absorber bottoms stream 52a and 40% of bottom stream 18 forming a second absorber bottoms stream 52'. First absorber bottoms stream 52a is heated in inlet exchanger 14 to −23° F. whereby it is partially vaporized, and sent to distillation tower 28 as a middle tower feed stream 52'. Second absorber bottoms stream 52' is sent directly to the top of distillation tower 28 as a top tower feed stream.

Absorber overhead stream 16, which is at −113° F., is a lean residue stream that is warmed to −90° F. in reflux exchanger 40 and then further warmed in front end exchanger 14 to 72° F. Warmed gas is compressed in booster compressor 48, which is driven by power generated by expander 30, to 433 psia. Intermediate pressure residue gas is sent to a residue compressor 49, where its pressure is raised to 618 psia to form residue gas stream 50. Residue gas stream 50 is a pipeline sales gas that contains substantially all of the methane and $C_2$ compounds in the inlet gas, and a minor portion of $C_3+$ compounds and heavier compounds.

Distillation tower 28 preferably is a reboiled absorber that operates at 420 psia. Distillation tower overhead temperature is −21° F., while the bottom is at 194° F. Distillation tower 28 is provided with an externally heated reboiler 58 that provides heating duty at the bottom of distillation tower 28 to reject ethane from distillation tower bottoms stream. Deethanizer bottoms stream 54 contains the major portion of $C_3+$ compounds that are desired to be recovered.

Simulations were performed using the process shown in FIG. 4 of the present invention. The results of the simulation are shown in Table V. In order to show the improvements in efficiency, feed conditions, composition, and residue conditions were the same as those used to demonstrate the efficiency of the processes described in U.S. Pat. No. 5,771,712. To further assist in comparing the present invention with the '712 prior art patent, table VI compares the results of the simulations performed on embodiments of the '712 patent shown in FIGS. 3–6 in the '712 patent compared to the embodiment illustrated in FIG. 4 of the present invention.

TABLE V

|  | MOL % | | |
| --- | --- | --- | --- |
| COMPONENT | FEED | RESIDUE | NGL |
| Methane | 93.726 | 95.123 | 0.000 |
| Ethane | 4.757 | 4.808 | 1.287 |
| Propane | 1.012 | 0.068 | 64.333 |
| i-Butane | 0.254 | 0.001 | 17.210 |
| n-Butane | 0.252 | 0.001 | 17.170 |
| Mol/hr | 86785 | 85511 | 1274 |
| Temperature (° F.) | 80 | 120 | 194 |

TABLE V-continued

| | MOL % | | |
|---|---|---|---|
| COMPONENT | FEED | RESIDUE | NGL |
| Pressure (psia) | 580 | 613 | 420 |
| C3 Recovery (%) | 93.4 | | |
| Residue Compression (hp) | 17294 | | |

TABLE VI

Figure 5:
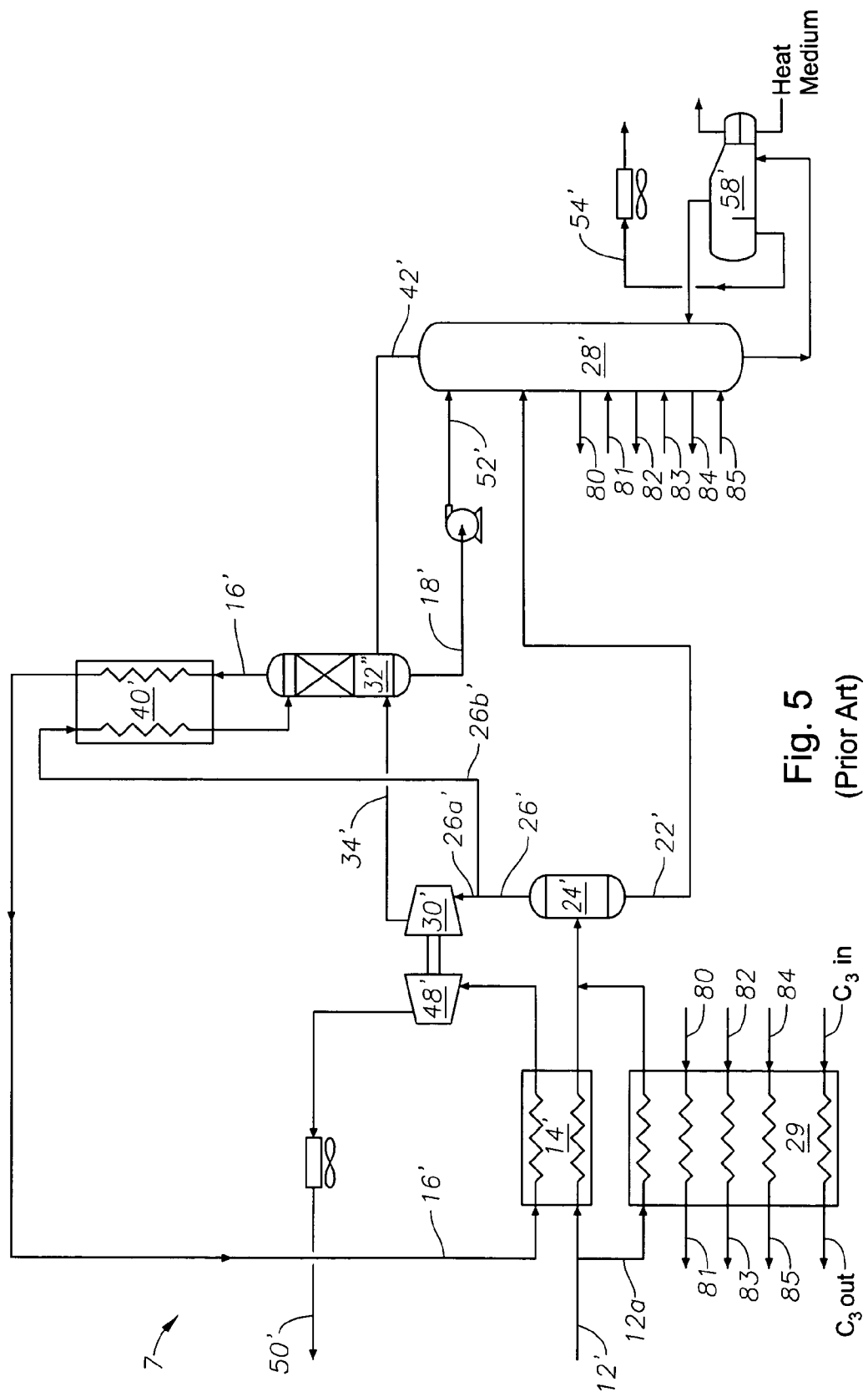
FIG. 5 is a simplified flow diagram of a prior art C2+ compound recovery process according to U.S. Pat. No. 4,157,904.
Figure 6:
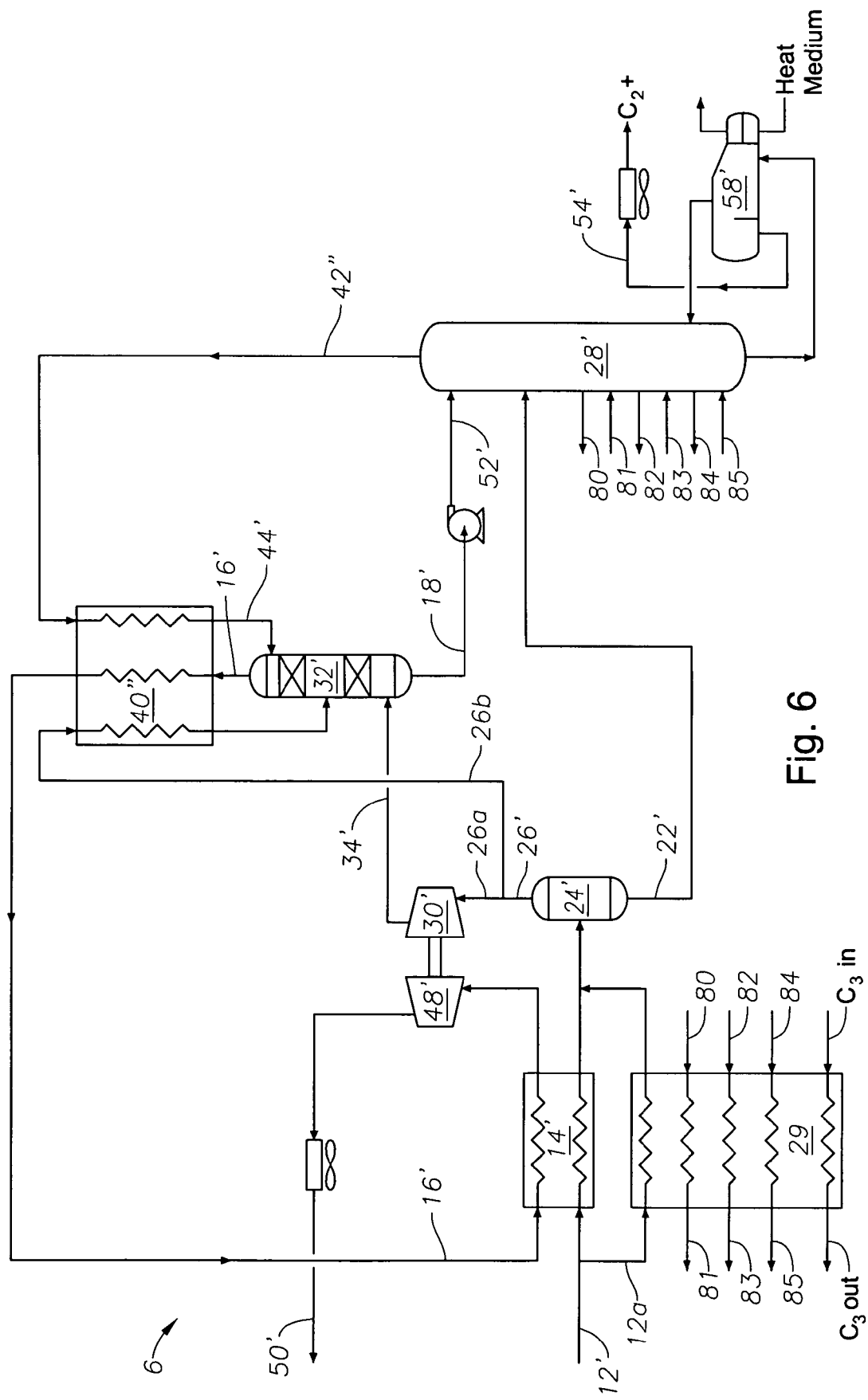
FIG. 6 is a simplified flow diagram of a new C2+ compound recovery process according to an alternate embodiment of the present invention.

| Scheme | Patent | C3 Recovery (%) | Residue Compression (hp) | Reboiler Duty MMBTU/hr |
|---|---|---|---|---|
| FIG. 3 | 4,617,039 | 93.7 | 21210 | 22.29 |
| FIG. 4 | 5,771,712 | 93.68 | 17536 | 16.27 |
| FIG. 5 | 5,771,712 | 93.72 | 17580 | 15.99 |
| FIG. 6 | 5,771,712 | 93.68 | 20215 | 20.25 |
| FIG. 4 | Present Invention | 93.4 | 17294 | 13.89 |

As can be seen in Table VI, the embodiment illustrated in FIG. 4 of the present invention has substantially lower residue compression and reboiler duty requirements than the FIGS. in the prior art patents listed in the table. In the process shown in FIG. 3 of U.S. Pat. No. 4,617,039 issued to Buck, the entire absorber bottoms stream, which is cold, is sent to the distillation column as a top tower feed stream, which results in the cold stream having to be reboiled at the bottom of the distillation column. The additional reboiler duty requirements increase the operating costs of this process embodiment and also make the process inefficient. In the process embodiments shown in FIGS. 4–6 of the '712 patent, the entire absorber bottoms stream is preheated and then sent to the distillation tower. This then reduces the reboiler duty requirements some, but the deethanizer overhead stream is warmer, which leads to an increase in the amount of components that are vaporized and leads to increased absorber overhead stream flow. Absorber overhead stream must then be condensed and returned to distillation tower. Hence this scheme is not efficient.

To reduce the reboiler requirements and simultaneously decrease absorber overhead stream flow, the present invention splits absorber bottoms stream into two streams, with one part, which is cold, being sent to the top of the distillation tower, and the other part being warmed to make the process more efficient.

In most cases, it is beneficial to split the feed stream to a distillation tower into two streams, with each stream having with different enthalpies. The stream with higher enthalpy is sent to the bottom of the tower, while the lower enthalpy stream is sent to the top of the tower. Operating the distillation tower in this manner is more efficient, which is evident from the results shown in the Table VI.

Figure 8:
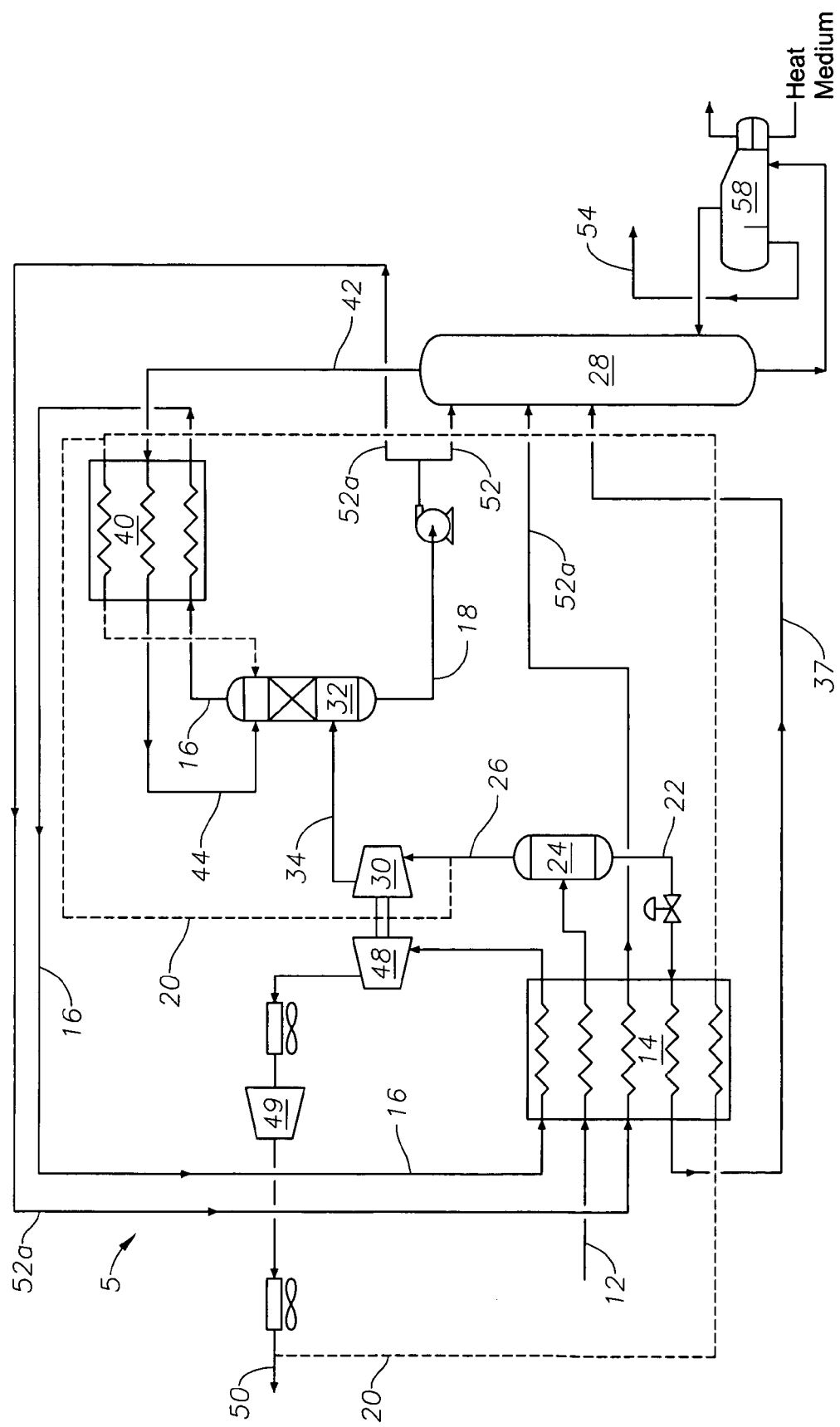
FIG. 8 is a simplified flow diagram of a two tower propane recovery process that has been modified for increased propane recovery by use of a second lean reflux stream with two sources for the second lean reflux streams that can be used separately or together, in accordance with an embodiment of the present invention.
Figure 9:
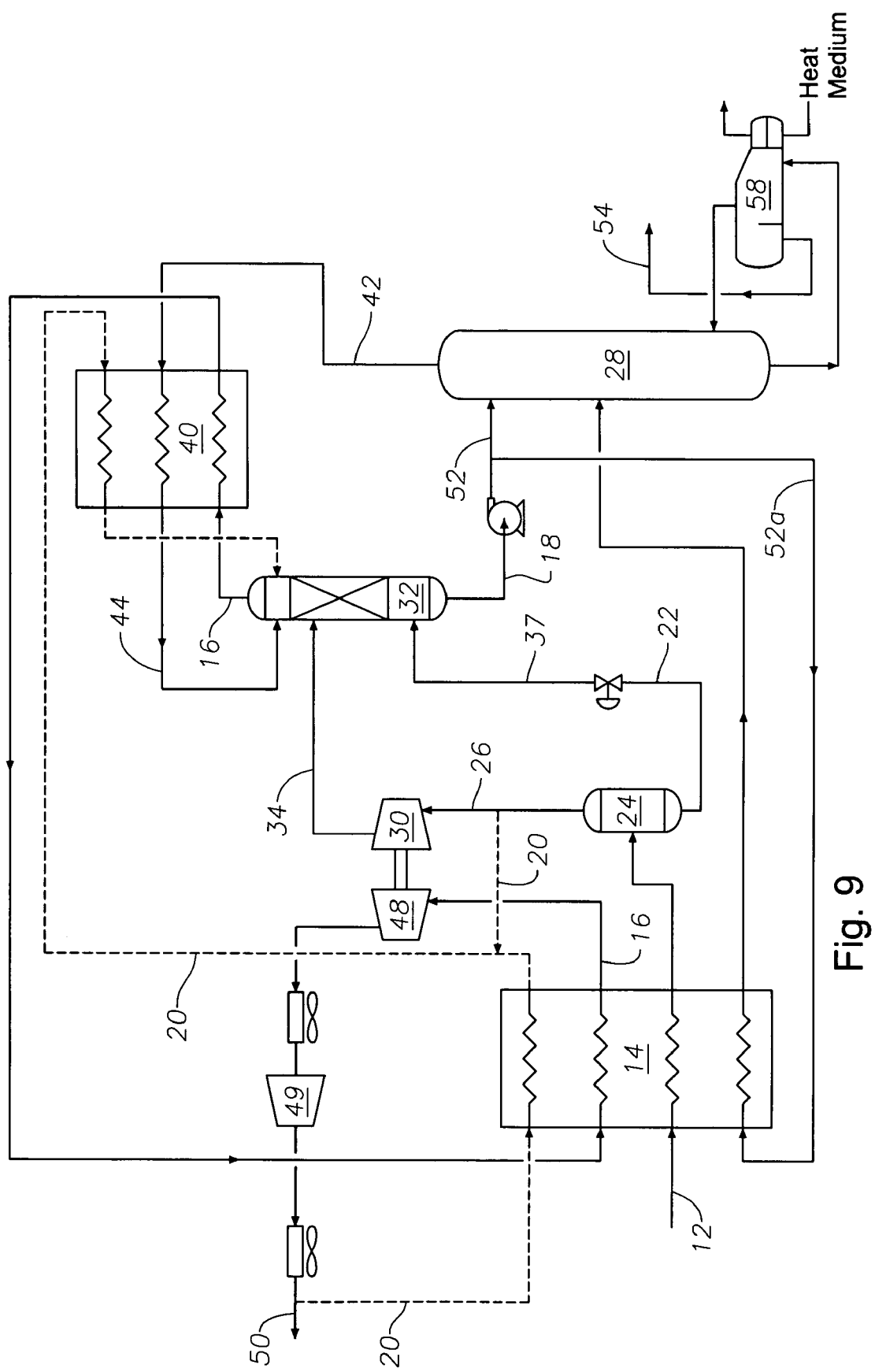
FIG. 9 is a simplified flow diagram of a two tower propane recovery process that has been simplified to reduce the number of heat exchanger passes in accordance with an embodiment of the present invention.

Alternate embodiments of the process shown in FIG. 4 that are designed to increase propane recovery are advantageously provided. For example, the addition of second lean reflux stream from residue gas stream or from a portion of cold separator vapor stream can be added to the process shown in the FIG. 4 scheme, as shown in FIGS. 8 and 9. These embodiments increase propane recovery, as described herein.

DETAILED DESCRIPTION OF SECOND PRIOR ART EXAMPLE

The present invention can be easily modified to allow users the option of recovering ethane and heavier compounds, as opposed to propane and heavier compounds. FIG. 5 illustrates a prior art ethane recovery process and apparatus 7 that can be used to recover ethane and heavier compounds.

Table VII shows the feed conditions for inlet gas stream that are used for the simulations for the processes shown in FIGS. 5 and 6.

TABLE VII

| Component | Mol % |
|---|---|
| N2 | 1.006 |
| CO2 | 0.083 |
| Methane | 82.926 |
| Ethane | 9.974 |
| Propane | 2.856 |
| i-Butane | 0.698 |
| n-Butane | 1.332 |
| i-Pentane | 0.333 |
| n-Pentane | 0.272 |
| n-Hexane | 0.128 |
| n-Octane | 0.026 |
| Temperature (° F.) | 80.6 |
| Pressure (psia) | 978.8 |
| Flow (MMSCFD) | 671.1 |

In the prior art arrangement shown in FIG. 5, an inlet gas stream 12' is cooled in inlet exchanger 14' by heat exchange contact with cold streams. Inlet gas stream 12' is then sent to a cold separator 24' that is used to separate the inlet gas stream 12' into a first liquid stream 22' and a first vapor stream 26'. First liquid stream 22' can be sent directly to demethanizer tower 28' as a first tower feed stream. First vapor stream 26' can be split into two streams, a first separator overhead stream 26a', which is 68.5% of the flow, and a second separator overhead stream 26b', which contains the remaining portion of the flow.

First separator overhead stream 26a' is expanded isentropically in expander 30' to 401 psia. Due to the reduction in pressure and the extraction of work from first separator overhead stream 26a', the stream is cooled to −90° F., thereby leading to partial condensation. This partially condensed stream 34' is then sent to an absorber column 32" as a lower absorber feed stream 34'. Second separator overhead stream 26b' is cooled to −121° F. and condensed in reflux exchanger 40' by heat exchange contact with cold streams, and sent to absorber column 32" as a top absorber feed stream. An absorber bottoms stream 18' at −95° F. is sent to demethanizer tower 28' as a top tower feed stream 52'. Absorber column 32" in this embodiment is a packed or trayed tower that operates at 396 psia. Vapor stream 16', or absorber overhead stream, produced at the top of absorber column 32" at −126° F. is a lean residue gas stream. Stream 16' is heated in reflux exchanger 40' to −45° F., and then further heated in inlet exchanger 14' to 38° F. Warm low pressure residue gas is then boosted in pressure in booster compressor 48' that runs off power generated by expander 30'. This intermediate pressure residue gas stream 50 is sent to residue gas compressors where its pressure is raised to 1020 psia. This high pressure residue gas stream is then sent for further processing.

Demethanizer tower 28' is a trayed or packed tower that produces a tower overhead stream 42' and a tower bottoms stream 54'. Tower overhead stream 42' at −93° F. is sent to absorber column 32", preferably at a lower absorber feed location as a reflux stream. Tower bottoms stream 54' at 88° F. contains the NGL stream product. FIG. 5 shows use of external propane refrigeration to cool the inlet gas stream, if needed. Use of this cooling medium depends on the feed conditions and composition, and may not always be required.

A simulation was performed using inlet gas stream 12' having a composition as shown in Table VII and the process illustrated in FIG. 5. The results of the simulation are shown in Table VIII.

TABLE VIII

|  | Feed | NGL Product |
|---|---|---|
| Flow | 671.1 MMSCFD | 65020 SBPD |
| C2 (mol %) | 9.974 | 55.496 |
| (ton/day) | 2405.76 | 1926.8 |
| C3 (mol %) | 2.856 | 19.535 |
| (ton/day) | 1010.11 | 995.6 |
| Residue Comp (hp) | 29384 | |
| C3 Refrig (mmbtu/hr) | 37.4 | |
| Plate Fin UA (Btu/F-hr) | 14.93E6 | |
| C2 Recovery (%) | 80.1 | |
| C3 Recovery (%) | 98.56 | |

As can be seen in Table VIII, some propane is lost from absorber column 32" due to the fact that the reflux stream 26b' contains propane, a portion of which will leave with residue gas stream 50' due to equilibrium limitations at the top of absorber column 32".

Absorber column 32" and distillation tower 28' can be arranged differently to increase ethane and propane recovery, without an increase in the compression power required to operate the process. A process with the revised two tower arrangement is shown in FIG. 6.

FIG. 6 illustrates an improvement to the prior art process illustrated in FIG. 5. As shown in FIG. 6, inlet gas stream 12' is cooled to −24° F. in inlet exchanger 14' by heat exchange contact with cold streams. Inlet gas 12' is then sent to a cold separator 24' that is used to separate the inlet gas stream 12' into a first liquid stream 22' and a first vapor stream 26'.

First liquid stream 22' can be sent directly to a demethanizer tower 28' as a first tower feed stream. First vapor stream 26' is split into two streams, a first separator overhead stream 26a which is 68.5% of the flow and a second separator overhead stream 26b which contains the remaining flow. First separator overhead stream 26a is isentropically expanded in expander 30' to 410 psia. Due to the reduction in pressure and extraction of work from stream 26a, expanded stream 34' exiting expander 30' is cooled to −89° F. and is partially condensed. This partially condensed stream 34' is then sent to an absorber column 32' as a bottom absorber feed stream 34'. In this embodiment, absorber column 32' includes one or more mass transfer zones, preferably two, within the vessel. Second separator overhead stream 26b is cooled to −122° F. and condensed in reflux exchanger 40" by heat exchange contact with cold streams. Second separator overhead stream 26b is then sent to absorber column 32' below at least a first mass transfer zone, and preferably between two mass transfer zones within absorber column 32'. Absorber bottoms stream 18' at −98° F. is sent to demethanizer tower 28' as top tower feed stream 52'. Absorber column 32' in this embodiment operates at 405 psia. Vapor stream, or absorber overhead stream, 16' produced at the top at −131° F. is lean residue gas. Stream 16' is heated in reflux exchanger 40' to −35° F., and then further heated in inlet exchanger 14' to 51° F. Warm low pressure residue gas is then boosted in pressure in booster compressor 48' that is runs off power generated by expander 30'. This intermediate pressure residue gas stream 50 is sent to residue gas compressors where its pressure is raised to 1020 psia. This high pressure residue gas stream has is then sent for further processing.

Demethanizer tower 28' produces a tower overhead stream 42" at −97° F. and a tower bottoms stream 54' at 84° F. Tower overhead stream 42" is cooled to −122° F. and partially condensed by heat exchange in reflux exchanger 40" and is sent to absorber column 32' as first lean reflux stream 44'. Tower bottoms stream 54' contains the NGL stream product.

As an advantage of the present invention, the amount of ethane recovered is about 5% greater and the amount of propane recovered is about 0.65% greater when compared with prior art ethane and propane recovery processes. These increases in recovery occur with the present invention without an increase in the residue gas compression requirements. Another advantage of the present invention is that the refrigeration duty is lowered by approximately 13%, which leads to lower operating costs for the process unit.

A simulation was performed using inlet gas stream 12' having a composition as shown in Table VII and the process illustrated in FIG. 6. The results of the simulation are shown in Table IX.

TABLE IX

|  | Feed | NGL Product |
|---|---|---|
| Flow | 671.1 MMSCFD | 67536 SBPD |
| C2 (mol %) | 9.974 | 56.35 |
| (ton/day) | 2405.76 | 2045 |
| C3 (mol %) | 2.856 | 18.82 |
| (ton/day) | 1010.11 | 1002 |
| Residue Comp (hp) | 29383 | |
| C3 Refrig (mmbtu/hr) | 33.1 | |
| Plate Fin UA (Btu/F-hr) | 21.8E6 | |
| C2 Recovery (%) | 85 | |
| C3 Recovery (%) | 99.2 | |

Figure 7:
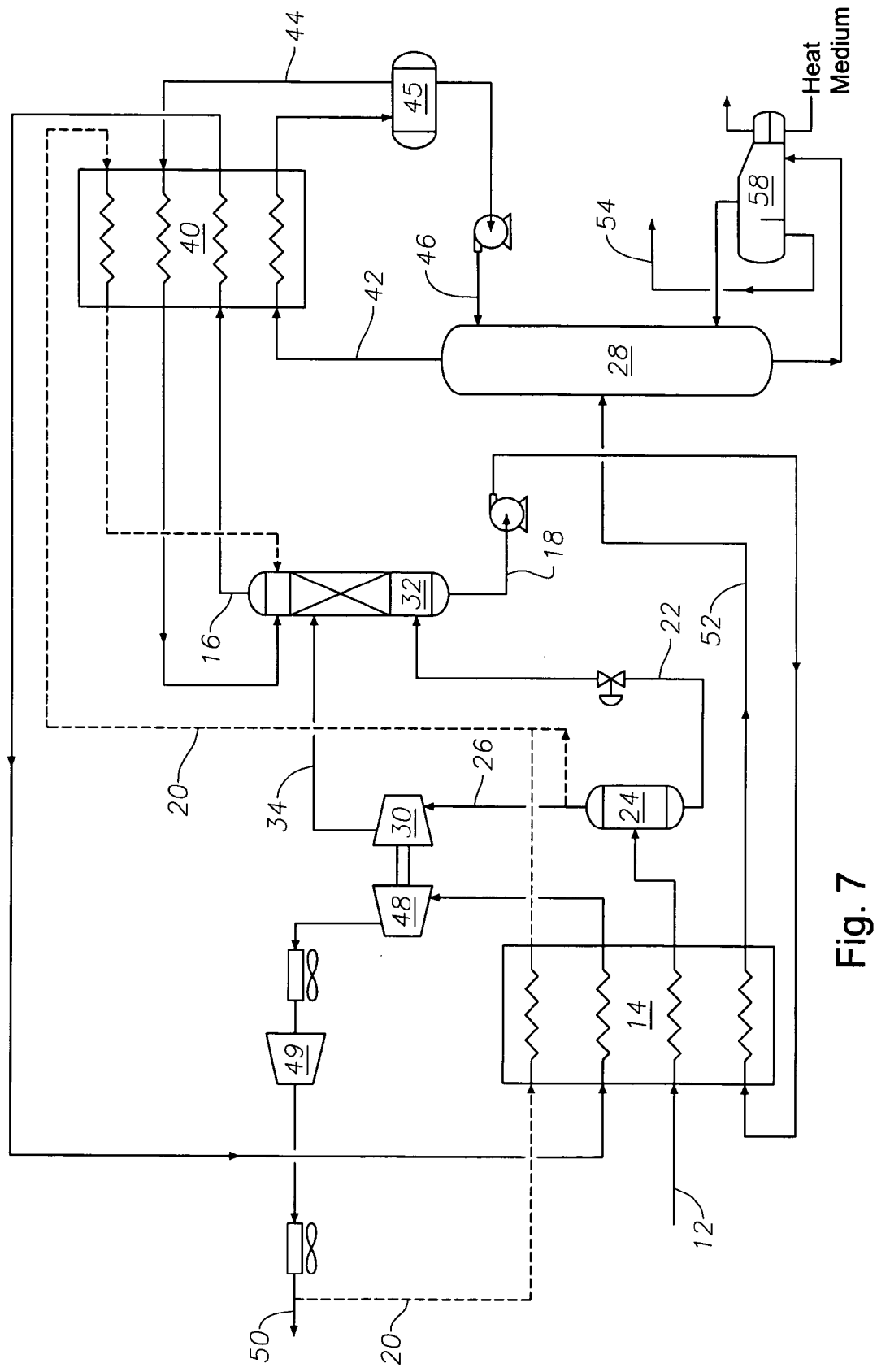
FIG. 7 is a simplified flow diagram of a two tower propane recovery process that has been simplified to reduce the number of heat exchanger passes and includes two sources of second lean reflux streams that can be used separately or together, in accordance with an embodiment of the present invention.

As can be seen in FIGS. 7–9, lean reflux stream 20 can have several sources, such as a portion of first vapor stream 26 or as a portion of residue gas stream 50. Cold separator bottoms stream 22 can also have alternate routes. For example, as shown in FIGS. 7 and 9, cold separator bottoms stream 22 can be sent to a bottom feed location of absorber column 32. Cold separator bottoms stream 22 can also be sent to distillation tower 28, as shown in FIG. 8.

In addition to the method embodiments, the apparatus to perform the methods described herein are advantageously provided. The apparatus for separating a gas stream containing methane, C2 and C3 components and heavier hydrocarbons into a volatile gas fraction containing substantially all of the methane and C2 components and a less volatile fraction containing a large portion of C3 components and heavier hydrocarbons preferably includes a first exchanger 14, a first separator 24, a distillation tower 28, a second exchanger 40, an expander 30, and a compressor 48.

First exchanger 14 is utilized for performing a process step selected from the group consisting of cooling a gas stream 12 to partially condense at least a portion of the gas stream 12, preheating at least a portion of a first liquid stream 22, preheating at least a portion of an absorber bottoms stream 18, heating an absorber overhead stream 16, cooling and at least partially condensing a portion of the residue gas stream 50 thereby producing a second lean reflux stream, and combinations thereof. External refrigerants such as propane or propylene can be used in the heat transfer process steps First separator 24 is used for separating inlet gas stream 12 into a first vapor stream 26 and at least first liquid stream 22. Distillation tower 28 is used for receiving a portion of the first liquid stream 22 as a lower tower feed stream and for receiving a portion of an absorber bottoms stream 18 as a middle tower feed stream. Distillation tower 28 advantageously produces a tower overhead stream 42 containing mainly methane and C2 components and a tower bottoms stream 54 containing a majority of the C3 components and heavier hydrocarbons. Distillation tower 28 can include trays or packing to assist in its distillation functions. Other suitable tower internals can be used, will be known to those of ordinary skill in the art, and are to be considered within the scope of the present invention.

Second exchanger 40 is for performing a process step selected from the group consisting of cooling the tower overhead stream 42 thereby producing a second vapor stream 44 and a liquid hydrocarbon stream 46, cooling and condensing at least a portion of the second vapor stream 44 thereby forming a first lean reflux stream, heating the absorber overhead stream 16, cooling and at least partially condensing the portion of the residue gas stream 50 thereby producing a second lean reflux stream 20.

Expander 30 expands the first vapor stream 26. Absorber column 32 preferably has at least one mass transfer zone. Absorber column 32 receives the first vapor stream 26 as a bottom absorber feed stream, the first lean reflux stream 44 as an absorber top feed stream, and the second lean reflux stream 20. Absorber column 32 produces an absorber overhead stream 16 containing essentially all methane, C2 and lighter components of the gas stream and the absorber bottoms stream 18.

As described previously, expander 30 can provide the power needed to operate compressor 48. Compressor 48 is used to compress absorber overhead stream 16 to produce a residue gas stream 50. Second separator 45 separates tower overhead stream 42 into a second vapor stream 44 and a liquid hydrocarbon stream 46.

When second lean reflux stream 20 is taken as a portion of residue gas stream 50, absorber column 32 includes at least one mass transfer zone. When second lean reflux stream 20 is taken as a portion of first vapor stream 26, absorber column 32 preferably has more than one mass transfer zone.

In some embodiments, a side feed stream 12a is taken from inlet gas stream 12. A third exchanger, or tower side reboiler, 29, cools side feed stream 12a. Tower side reboiler 29 can be used for performing a process step selected from the group consisting of cooling at least a portion of the gas stream, warming at least one tower reboiler side stream, and combinations thereof. Tower side reboiler 29 can be a single exchanger or a plurality of exchangers, depending upon the required reboiler duty for distillation tower 28. External refrigerants, such as propane or propylene, can be used, if needed. Each tower reboiler side stream 80, 82, 84 is warmed by heat exchange contact with side feed stream 12a, which is simultaneously being cooled, and is returned to distillation tower 28 as return side streams 81, 83, 85.

In some embodiments, second separator 45 can be used to separate tower overhead stream 42 into second vapor stream, or first lean reflux stream, 44 and a liquid hydrocarbon stream 46. Lean reflux stream 44 is sent to absorber column 32 and liquid hydrocarbon stream is sent to distillation tower 28.

As another advantage of the present invention, the processes can be easily converted between propane and heavier compound recovery and ethane and heavier compound recovery to allow users to recover the more valuable of the two compounds, based upon market conditions. The flexibility allows users to maximize the market conditions to their favor, which typically maximizes profits.

While the invention has been shown or described in only some of its forms, it should be apparent to those skilled in the art that it is not so limited, but is susceptible to various changes without departing from the scope of the invention.

For example, various means of heat exchange can be used to supply the deethanizer tower reboiler with heat. The reboiler can be more than one exchanger or be a single multi-pass exchanger. Equivalent types of reboilers will be known to those skilled in the art. As another example, the expanding steps, preferably by isentropic expansion, may be effectuated with a turbo-expander, Joule-Thompson expansion valves, a liquid expander, a gas or vapor expander or the like. Also, the expanders may be linked to corresponding staged compression units to produce compression work by substantially isentropic gas expansion.

We claim:

1. A process for separating a gas stream containing methane, C2 and C3 components and heavier hydrocarbons into a volatile gas fraction containing substantially all of the methane and C2 components and a less volatile fraction containing a large portion of C3 components and heavier hydrocarbons, the process comprising the steps of:
   a. supplying and cooling a gas stream to partially condense at least a portion of the gas stream to produce a first vapor stream and at least a first liquid stream;
   b. preheating at least a portion of the first liquid stream and then sending the portion of the first liquid stream to a distillation tower, the distillation tower producing a tower overhead stream containing mainly methane and C2 components and a tower bottoms stream containing a majority of the C3 components and heavier hydrocarbons;
   c. cooling and partially condensing the tower overhead stream thereby producing a second vapor stream and a liquid hydrocarbon stream, the liquid hydrocarbon stream being sent to the distillation tower as a top feed;
   d. expanding the first vapor stream and sending the first vapor stream to an absorber column having at least one mass transfer zone as a bottom absorber feed streamthereby producing an absorber overhead stream containing essentially all methane, C2 and lighter components of the gas stream and an absorber bottoms stream;
   e. preheating at least a portion of the absorber bottoms stream and sending the portion of the absorber bottoms stream into the distillation tower as a middle tower feed stream;
   f. cooling and condensing at least a portion of the second vapor stream thereby forming a first lean reflux stream and sending the first lean reflux stream to the absorber as an absorber top feed stream;
   g. heating the absorber overhead stream, compressing, and discharging the absorber overhead stream as a residue gas stream; and
   h. wherein the improvement comprises cooling and at least partially condensing the portion of the residue gas stream thereby producing a second lean reflux stream and then sending the second lean reflux stream to the absorber column.

2. The process according to claim 1, wherein the improvement comprises sending the first lean reflux stream to the absorber column at a feed location below that of the second lean reflux stream.

3. The process according to claim 1, wherein the improvement comprises combining the first and second lean reflux streams prior to sending the streams to the absorber column.

4. The process according to claim 1, wherein the improvement comprises sending the second lean reflux stream to a top of the absorber column.

5. The process according to claim 1, wherein the steps of cooling the gas stream, preheating at least a portion of the first liquid stream, preheating at least a portion of the absorber bottoms stream, heating the absorber overhead stream, and cooling a portion of the residue gas stream are performed by providing heat exchange contact with a process stream selected from the group consisting of the absorber overhead stream, the absorber bottoms stream, the first liquid stream, the portion of the residue gas stream, the gas stream, an external refrigerant stream, and combinations thereof.

6. The process according to claim 1, wherein the step of sending the portion of the first liquid stream to the distillation tower includes sending the portion of the first liquid stream as a lower tower feed stream.

7. The process according to claim 1, wherein the steps of cooling and partially condensing the tower overhead stream include sending the liquid hydrocarbon stream to the distillation tower as a top tower feed stream.

8. The process according to claim 1, wherein the step of sending the first vapor stream to the absorber column includes sending the first vapor stream as a bottom absorber feed stream.

9. The process according to claim 1, wherein the step of sending the portion of the absorber bottoms stream to the distillation column includes sending the portion of the absorber bottoms stream as a middle tower feed stream.

10. The process according to claim 1, wherein the steps of heating the absorber overhead stream, cooling a portion of the residue gas stream, cooling the tower overhead stream, and cooling at least a portion of the second vapor stream are performed by providing heat exchange contact with a process stream selected from the group consisting of the absorber overhead stream, the portion of the residue gas stream, the tower overhead stream, and the portion of the second vapor stream, and combinations thereof.

11. A process for separating a gas stream containing methane, C2 and C3 components and heavier hydrocarbons into a volatile gas fraction containing substantially all of the methane and C2 components and a less volatile fraction containing a large portion of C3 components and heavier hydrocarbons, the process comprising the steps of:
  a. supplying and cooling a gas stream to partially condense at least a portion of the gas stream to produce a first vapor stream and at least a first liquid stream containing some lighter components;
  b. preheating at least a portion of the first liquid and then sending the portion of the first liquid stream to a distillation tower, the distillation tower producing a tower overhead stream containing mainly methane and C2 components and a tower bottoms stream containing a majority of the C3 components and heavier hydrocarbons;
  c. cooling and partially condensing the tower overhead stream thereby producing a second vapor stream and a liquid hydrocarbon stream;
  d. sending the liquid hydrocarbon stream to the distillation tower;
  e. expanding the first vapor stream and sending the first vapor stream to an absorber column having at least one mass transfer zone as a bottom feed stream thereby producing an absorber overhead stream containing essentially all methane, C2, and lighter components of the gas stream and an absorber bottoms stream;
  f. preheating at least a portion of the absorber bottoms stream and directing the portion of the absorber bottoms stream into the distillation tower;
  g. condensing at least a portion of the second vapor stream thereby forming a first lean reflux stream and sending the first lean reflux stream to the absorber;
  h. heating and compressing the absorber overhead stream to produce a residue gas stream; and
  i. wherein the improvement comprises cooling and at least partially condensing a portion of the first vapor stream thereby producing a second lean reflux stream and then sending the second lean reflux stream to the absorber column.

12. The process according to claim 11, wherein the improvement comprises sending the second lean reflux stream to a feed location located at least one mass transfer zone below that of the first lean reflux stream.

13. The process according to claim 11, wherein the improvement comprises sending the first lean reflux stream to a top of the absorber column.

14. The process according to claim 11, wherein the step of sending the portion of the first liquid stream to the distillation tower includes sending the portion of the first liquid stream to the distillation tower as a lower tower feed stream.

15. The process according to claim 11, wherein the step of sending the liquid hydrocarbon stream to the distillation tower includes sending the liquid hydrocarbon stream to the distillation tower as a top feed stream.

16. A process for separating a gas stream containing methane, C2 and C3 components and heavier hydrocarbons into a volatile gas fraction containing substantially all of the methane and C2 components and a less volatile fraction containing a large portion of C3 components and heavier hydrocarbons, the process comprising the steps of:
  a. supplying and cooling a gas stream to partially condense at least a portion of the gas stream to produce a first vapor stream and at least a first liquid stream containing some lighter components;
  b. expanding the first vapor stream and sending the first vapor stream to an absorber column having at least one mass transfer zone as a bottom feed stream thereby producing an absorber overhead stream containing essentially all methane, C2 and lighter components of the gas stream and an absorber bottoms stream;
  c. expanding at least the first liquid stream and feeding the first liquid stream to the absorber column 32;
  d. preheating at least a portion of the absorber bottoms stream and sending the portion of the absorber bottoms stream to a distillation tower the distillation tower producing a tower overhead stream containing mainly methane and C2 components and a tower bottoms stream containing a majority of the C3 components and heavier hydrocarbons;
  e. cooling and partially condensing the tower overhead stream thereby producing a second vapor stream and a liquid hydrocarbon stream, the liquid hydrocarbon stream being directed to the distillation tower as a top feed;
  f. condensing at least a portion of second vapor stream thereby forming a first lean reflux stream and sending the first lean reflux stream to the absorber column;
  g. heating the absorber overhead stream, compressing, and discharging the absorber overhead stream as residue gas; and h. wherein the improvement comprises cooling and at least partially condensing the portion of the residue gas thereby producing a second lean reflux stream and then sending the second lean reflux stream to the absorber column. Make sending to top of the absorber a dependent claim.

17. The process according to claim 16, wherein the improvement comprises sending the first lean reflux stream to a feed location below that of the second lean reflux stream.

18. The process according to claim 16, wherein the improvement comprises sending the first lean reflux stream to a top of the absorber column.

19. The process according to claim 16, wherein the step of feeding the first liquid stream to the absorber column 32 includes feed the first liquid stream to a feed location located below that of the expanded first vapor stream.

20. The process according to claim 16, wherein the step of sending the portion of the absorber bottoms stream to a distillation tower includes sending the portion of the absorber bottoms stream to the distillation tower as a bottom feed stream.

21. A process for separating a gas stream containing methane, C2 and C3 components and heavier hydrocarbons into a volatile gas fraction containing substantially all of the methane and C2 components and a less volatile fraction containing a large portion of C3 components and heavier hydrocarbons, the process comprising the steps of:
   a. supplying and cooling a gas stream to partially condense at least a portion of the gas stream to produce a first vapor stream and at least a first liquid stream;
   b. expanding the first vapor stream and sending the first vapor stream to an absorber column having at least one mass transfer zone thereby producing an absorber overhead stream containing essentially all methane, C2 and lighter components of the gas stream and an absorber bottoms stream;
   c. expanding at least the first liquid stream and feeding the first liquid stream to the absorber;
   d. preheating at least a portion of the absorber bottoms stream and sending the portion of the absorber bottoms stream to a distillation tower, the distillation tower producing a tower overhead stream containing mainly methane and C2 components and a tower bottoms stream containing a majority of the C3 components and heavier hydrocarbons;
   e. cooling and partially condensing the tower overhead stream thereby producing a second vapor stream and a liquid hydrocarbon stream;
   f. sending the liquid hydrocarbon stream to the distillation tower;
   g. condensing at least a portion of the second vapor stream thereby forming a first lean reflux stream and sending the first lean reflux stream to the absorber column;
   h. heating and compressing the absorber overhead stream to produce a residue gas stream; and
   i. wherein an improvement comprises cooling and at least partially condensing a portion of the first vapor stream thereby producing a second lean reflux stream and then sending the second lean reflux stream to the absorber column.

22. The process according to claim 21, wherein the improvement comprises sending the second lean reflux stream to a feed location located at least one mass transfer zone below that of the first lean reflux stream.

23. The process according to claim 21, wherein the improvement comprises sending the second lean reflux stream to a top of the absorber column.

24. The process according to claim 21, wherein the step of sending the first vapor stream to an absorber column includes sending the first vapor stream as a bottom feed stream.

25. The process according to claim 21, wherein the step of sending the liquid hydrocarbon stream to the distillation tower includes sending the liquid hydrocarbon stream to the distillation column as a top tower feed stream.

26. A process for separating a gas stream containing methane, C2 and C3 components and heavier hydrocarbons into a volatile gas fraction containing substantially all of the methane and C2 components and a less volatile fraction containing a large portion of C3 components and heavier hydrocarbons, the process comprising the steps of:
   a. supplying and cooling a gas stream to partially condense at least a portion of the gas stream to produce a first vapor stream and at least a first liquid stream containing some lighter components;
   b. preheating at least a portion of the first liquid and then sending the portion of the first liquid into a distillation tower as a lower tower feed stream, the distillation tower producing a tower overhead stream containing mainly methane and C2 components and a tower bottoms stream containing a majority of the C3 components and heavier hydrocarbons;
   c. expanding the first vapor stream and sending the first vapor stream to an absorber column having at least one mass transfer zone thereby producing an absorber overhead stream containing essentially all methane, C2 and lighter components of the gas stream and an absorber bottoms stream;
   d. sending at least a portion of the tower overhead stream to the absorber column as a first lean reflux stream;
   e. heating and compressing the absorber overhead stream to produce a residue gas stream; and
   f. wherein an improvement comprises preheating a first portion of the absorber bottoms stream and sending the first portion of the absorber bottoms stream to the distillation tower, and sending a second portion of the absorber bottoms stream to the distillation tower.

27. The process according to claim 26, wherein the improvement further comprises sending the first portion of the absorber bottoms stream to a lower feed location that that of the second portion of the absorber bottoms stream.

28. A process for separating a gas stream containing methane, C2 and C3 components and heavier hydrocarbons into a volatile gas fraction containing substantially all of the methane and C2 components and a less volatile fraction containing a large portion of C3 components and heavier hydrocarbons, the process comprising the steps of:
   a. supplying and cooling a gas stream to partially condense at least a portion of the gas stream to produce a first vapor stream and at least a first liquid stream containing some lighter components;
   b. expanding the first vapor stream and sending the first vapor stream to an absorber column having at least one mass transfer zone thereby producing an absorber overhead stream containing essentially all methane, C2 and lighter components of the gas stream and an absorber bottoms stream;
   c. expanding at least the first liquid stream and feeding the first liquid stream to the absorber column;
   d. preheating at least a portion of the absorber bottoms stream and sending the portion of the absorber bottoms stream to a distillation tower, the distillation tower producing a tower overhead stream containing mainly methane and C2 components and a tower bottoms stream containing a majority of the C3 components and heavier hydrocarbons;

e. condensing at least a portion of a tower overhead stream and sending it to the absorber column as a first lean reflux stream;

f. heating the absorber overhead stream, compressing, and discharging the absorber overhead stream as a residue gas; and g. wherein an improvement comprises preheating a first portion of the absorber bottoms stream and sending the portion of the absorber bottoms stream to the distillation tower, and sending a second portion of the absorber bottoms stream to the distillation tower.

29. The process according to claim 28, wherein the improvement further comprises sending the first portion of the absorber bottoms stream at a lower feed location than that of the second portion of the absorber bottoms stream.

30. The process according to claim 28, wherein the step of feeding the first liquid stream to the absorber column includes feeding the first liquid stream at a feed location located below that of the expanded first vapor stream.

31. The process according to claim 28, wherein the improvement further comprises cooling and at least partially condensing a portion of the residue gas stream thereby producing a second lean reflux stream and then sending the second lean reflux stream to the absorber column.

32. The process according to claim 31, wherein the first lean reflux stream is introduced at a feed location located below that of the second lean reflux stream.

33. The process according to claim 31, wherein the second lean reflux stream is sent to a top of the absorber column.

34. A process for separating a gas stream containing methane, C2 and C3 components and heavier hydrocarbons into a volatile gas fraction containing substantially all of the methane and C2 components and a less volatile fraction containing a large, portion of C3 components and heavier hydrocarbons, the process comprising the steps of:

a. supplying and cooling a gas stream to partially condense at least a portion of the gas stream to produce a first vapor stream and at least a first liquid stream containing some lighter components;

b. expanding the first vapor stream and sending the first vapor stream to an absorber column having at least one mass transfer zone thereby producing an absorber overhead stream containing essentially all methane, C2 and lighter components of the gas stream and an absorber bottoms stream;

c. expanding at least the first liquid stream and feeding the first liquid stream to the absorber column;

d. preheating at least a portion of the absorber bottoms stream and sending the portion of the absorber bottoms stream to a distillation tower, the distillation tower producing a tower overhead stream containing mainly methane and C2 components and a tower bottoms stream containing a majority of the C3 components and heavier hydrocarbons;

e. condensing at least a portion of the tower overhead stream and sending it to the absorber column as a first lean reflux stream;

f. heating and compressing the absorber overhead stream to produce a residue gas stream; and g. wherein an improvement comprises cooling and at least partially condensing a portion of the first vapor stream thereby producing a second lean reflux stream and then sending the second lean reflux stream to the absorber column.

35. The process according to claim 34, wherein the second lean reflux stream is sent to the absorber column at a feed location located at least one mass transfer zone below that of the first lean reflux stream.

36. The process according to claim 34, wherein the step of feeding the first liquid stream to the absorber column includes feeding the first liquid stream to a feed location located below that of the expanded first vapor stream.

37. The process according to claim 34, wherein the second lean reflux stream is sent to a top of the absorber column.

38. A process for separating a gas stream containing methane, C2 and C3 components and heavier hydrocarbons into a volatile gas fraction containing substantially all of the methane components and a less volatile fraction containing a large portion of C2 components and heavier hydrocarbons, the process comprising the steps of:

a. supplying and cooling a gas stream to partially condense at least a portion of the gas stream to produce a first vapor stream and at least a first liquid stream containing some lighter components;

b. sending the first liquid stream to a distillation tower, the distillation tower producing a tower overhead stream containing mainly methane components and a tower bottoms stream containing a majority of the C2 components and heavier hydrocarbons;

c. splitting the first vapor stream into a first separator overhead stream and a second overhead stream;

d. expanding and sending the first separator overhead stream to an absorber column having at least one mass transfer zone thereby producing an absorber overhead stream containing essentially all methane and lighter components of the gas stream and an absorber bottoms stream;

e. cooling the second separator overhead stream and sending the second separator overhead stream to the absorber column;

f. heating and compressing the absorber overhead stream to produce a residue gas stream; and g. wherein an improvement comprises condensing at least a portion of the tower overhead stream thereby producing a first lean reflux stream and sending the first lean reflux stream to the absorber.

39. The process according to claim 38, wherein the improvement further includes sending the first lean reflux stream to the absorber to a feed location located below at least the first mass transfer zone.

40. The process according to claim 38, wherein the step of cooling the gas stream includes cooling at least a portion of the gas stream by heat exchange contact with at least one tower side stream thereby heating the at least one tower side stream prior to being sent back to the distillation column.

41. An apparatus for separating a gas stream containing methane, C2 and C3 components and heavier hydrocarbons into a volatile gas fraction containing substantially all of the methane and C2 components and a less volatile fraction containing a large portion of C3 components and heavier hydrocarbons, the apparatus comprising:

a. a first exchanger for performing a process step selected from the group consisting of cooling a gas stream to partially condense at least a portion of the gas stream, preheating at least a portion of a first liquid stream, preheating at least a portion of an absorber bottoms stream, heating the absorber overhead stream, cooling and at least partially condensing the portion of the residue gas stream thereby producing a second lean reflux stream, and combinations thereof;

b. a first separator for separating the gas stream into a first vapor stream and at least the first liquid stream;

c. a distillation tower for receiving the portion of the first liquid stream as a lower tower feed stream and for receiving a portion of an absorber bottoms stream as a middle tower feed stream, the distillation tower producing a tower overhead stream containing mainly methane and C2 components and a tower bottoms stream containing a majority of the C3 components and heavier hydrocarbons;

d. a second exchanger for performing a process step selected from the group consisting of cooling the tower overhead stream thereby producing a second vapor stream and a liquid hydrocarbon stream, cooling and condensing at least a portion of the second vapor stream thereby forming a first lean reflux stream, heating the absorber overhead stream, cooling and at least partially condensing the portion of the residue gas stream thereby producing a second lean reflux stream e. an expander for expanding the first vapor stream;

f. an absorber column having at least one mass transfer zone for receiving the first vapor stream as a bottom absorber feed the stream the first lean reflux stream as an absorber top feed stream, and the second lean reflux stream, the absorber column thereby producing an absorber overhead stream containing essentially all methane, C2 and lighter components of the gas stream and the absorber bottoms stream; and g. a compressor for compressing the absorber overhead stream to produce a residue gas stream.

42. The apparatus of claim 41, including a second separator for separating the tower overhead stream into a second vapor stream and a liquid hydrocarbon stream.

43. The apparatus of claim 41, wherein the absorber comprises at least one mass transfer zone.

44. The apparatus of claim 41, wherein the absorber comprises more than one mass transfer zone.

45. The apparatus of claim 41, further comprising a third exchanger for performing a process step selected from the group consisting of cooling at least a portion of the gas stream, warming at least one tower reboiler side stream, and combinations thereof.

* * * * *